(12) United States Patent
Taparia

(10) Patent No.: US 11,648,147 B2
(45) Date of Patent: May 16, 2023

(54) INSTRUMENT TO PREPARE AN INTRA-UTERINE DEVICE FOR INSERTION

(71) Applicant: Pregna International Limited, Mumbai (IN)

(72) Inventor: Mukul Taparia, Mumbai (IN)

(73) Assignee: Pregna International Limited, Mumbai (IN)

( * ) Notice: Subject to any disclaimer, the term of this patent is extended or adjusted under 35 U.S.C. 154(b) by 100 days.

(21) Appl. No.: 16/936,613

(22) Filed: Jul. 23, 2020

(65) Prior Publication Data

US 2021/0030585 A1 Feb. 4, 2021

(30) Foreign Application Priority Data

Jul. 31, 2019 (IN) .............................. 201921030966

(51) Int. Cl.
*A61F 6/14* (2006.01)
*A61F 6/18* (2006.01)

(52) U.S. Cl.
CPC ................ *A61F 6/18* (2013.01); *A61F 6/144* (2013.01)

(58) Field of Classification Search
CPC .... A61F 6/18; A61F 6/144; A61F 6/14; A61F 6/005; A61F 6/142; A61F 6/12; A61B 18/1485; A61B 17/0218; A61B 17/42; A61B 2017/00577; A61B 2017/00505; A61B 2017/00559
See application file for complete search history.

(56) References Cited

U.S. PATENT DOCUMENTS 3,797,493 A * 3/1974 Saudek .................. B65D 75/68
 604/408
4,549,652 A * 10/1985 Free ........................ A61F 6/005
 206/363
5,370,129 A * 12/1994 Diaz ......................... A61F 6/18
 128/839

FOREIGN PATENT DOCUMENTS

DE 2506890 B1 * 5/1976

* cited by examiner

*Primary Examiner* — Camtu T Nguyen

(57) ABSTRACT

An instrument 10 to prepare an intra-uterine device 30 for insertion in uterus 50 of woman, comprising a downfolding device 20, a graduated tube 16, a push rod 17, a stopper 15, and an IUD 30; the downfolding device 20 having a concave depression 41 on either side, an open channel 29 of a circular orifice 46 having a sector of angle measure 46A at least 220° and having an exit opening 48 initially marginally less than an external diameter 22B of the graduated tube 16, a root thickness 37B of the base 37 in-between the open channel 29 such that the exit opening 48 increases by the base 37 flexing; the graduated tube 16 has an internal diameter 22D of a far-end opening 22a of the graduated tube 16 sufficient to capture the stem 33 and both arms 32 of the IUD 30 in a downward triangular formation 51.

8 Claims, 21 Drawing Sheets

INSTRUMENT TO PREPARE AN INTRA-UTERINE DEVICE FOR INSERTION

FIELD OF THE INVENTION

The present invention relates to intra-uterine device, particularly to an instrument which is to load and insert intra-uterine device and the process of loading and inserting the intra-uterine device hygienically.

BACKGROUND OF THE INVENTION

There are several female contraceptives available. Intra-uterine device (herein after abbreviated as IUD) is a long- or medium-term contraceptive which is placed in the uterus of female. Most commonly available IUDs are in the shape of the English letter "T" since this shape is found appropriate to the shape of uterus.

While the IUDs are required to be in the shape of "T", they cannot be inserted in this form as the opening of the cervix is small. Arms forming "T" of IUD are folded either upwards or downwards so that IUD can be contained in the opening of a narrow tube which then can be inserted in the uterus. This process of folding the IUD so that the instrument is ready to insert is known as loading or preparing the IUD.

Loading or preparing of IUD needs to be done minutes before it is required to be inserted in uterus, and if done earlier, or if supplied duly loaded, then the IUD shall not return to the desired "T" shape in uterus, and shall not work effectively. Due to this requirement, the process of loading has to be performed by service providers just prior to inserting and placing IUD in uterus.

Up-folding IUDs and down-folding IUD have a significant difference in their preparation. Upfolding IUDs implies that arms forming "T" are together while stem of IUD is below folded arms. This may be easily understood from FIGS. 1A to 3B of Patent US005785053A. Patent application US2013/0014762(A1) also comprehensively covers an upfolding IUD. Down-folding implies that arms forming "T" as well as stem of IUD are together. This may be easily understood from FIGS. 7 and 9 of U.S. Pat. No. 4,143,656.

There is a significant difference in process of inserting and placing an up-folding IUD and a down-folding IUD in uterus. While placing an upfolding IUD, the arms of the T start unfolding downwards as soon as IUD is made to gradually eject out of the instrument. Person placing such upfolding IUD takes a pause to allow the upfolding arms to unfold at their own pace before finally placing IUD in uterus, lest ends of arms of IUD gets entangled with side walls of uterus, preventing a far end of IUD to reach fundus! On the other hand, when placing a downfolding IUD, there is no such precaution needed as the arms of IUD unfold upwards at their own natural pace while a far end of the IUD touches fundus.

In other words, an upfolding IUD is easier to load and difficult to place in uterus, while a downfolding IUD is relatively more difficult to load and relatively easier to place.

Patent application Ser. No. 15/745,579 discloses an instrument to load a downfold IUD without human maneuvering.

Such instruments being for one-time use, cost is an important factor.

Present invention effectively and economically addresses loading or preparation of downfolding IUDs for subsequent insertion and placement in uterus.

OBJECTIVES

The objective is to invent an instrument to load or prepare the intra-uterine device hygienically.

Another objective is to invent a simple instrument to load or prepare the intra-uterine device which is downfoldable.

Yet another objective is to invent an instrument which is capable of loading the intra uterine device in a consistent manner.

Yet another objective is to invent an instrument that causes minimal insertion trauma to woman.

Yet another objective is to invent an instrument which is economical and effective.

SUMMARY OF INVENTION

The instrument according to present invention comprises a downfolding device, a graduated tube, a push rod, a stopper, and an intra-uterine device generally known as an IUD, encased in a transparent pouch.

The IUD is essentially in a "T" shape, comprising a molded frame having a metallic envelope/wire wrapped around a stem, preferably with a sleeve on each of a pair of arms. The sleeve is generally made of medical grade copper.

The downfolding device has a fence and an open channel, spaced by a platform, on a base. An external side of the fence has a depression on either side, a concave, and generally complementary to a convex shape of human thumb and human fingers and therefore acts as a receptacle; consequently a service provider can hold the downfolding device firmly and which facilitates easy and secure loading of IUD into the graduated tube. An internal side of the fence has a converging opening, turning into a narrow zone and ending into a well having a depth. The narrow zone has a projecting ridge on either side, leaving a clear passage. The well has an orienting step on either side. The open channel has a circular orifice having a sector of angle measure at least 220°. The circular orifice merges with a pair of divergent walls, having an exit opening that is initially marginally less than an external diameter of the graduated tube. A root thickness of the base in-between the open channel is minimal. Consequently, the exit opening increases by the base flexing and or when a lower surface of the base is devoid of a firm support underneath. An upper enveloping surface all over the downfolding device is a smoothened surface devoid of sharp projection.

The graduated tube has an internal diameter of a far-end opening of the graduated tube just sufficient to capture the stem and both arms of the IUD in substantially a downward triangular formation. The downward triangular formation is attainable by entering a downfolded IUD in a graduated tube from the stem end such that the arm ends subsequently enter the graduated tube with a minimal force such that the arm ends are inside a graduated tube up to the step of the sleeve on the IUD. Also, the graduated tube is provided with measurement marks so that the stopper can be conveniently adjusted at precisely required position without needing measurement device and while the instrument is in the transparent pouch.

The IUD is parked in the downfolding device with its arms resting at the platform and the stem passing through the open channel of the downfolding device. The instrument is packaged in sterile environment in the transparent pouch with a transparent cover and a back. As a variation, the packaged instrument is sterilized after packaging.

The transparent pouch is made of a thermoplastic sheath of thickness such that the downfolding device when gripped firmly from an outside of the transparent cover of the transparent pouch can be gripped adequately. The upper enveloping surface all over the downfolding device, being a smoothened surface devoid of sharp projection, facilitates such ripping without the thermoplastic sheath getting punctured or torn consequently. A shear strength of the thermoplastic sheath withstands expected transportation and storage abuse.

To start the process of loading, the transparent cover is partially separated from the back of the transparent pouch, only to be able to access and hold the near end opening of graduated tube. The downfolding device is firmly held by one hand from outside the transparent cover while the graduated tube is pushed in.

As the graduated tube starts pushing the IUD, the IUD has to negotiate its shape due to the converging opening in the downfolding device. Consequently, the arms of the IUD start folding towards the stem end, such partially folded arms. The downfolding device guides the graduated tube through towards the well consequent to the open channel.

The depth of the well of the well of the downfolding device is such that, as the graduated tube continues to push the IUD, there comes a situation when a fundal end of the IUD gets stopped by the of the well, and the arms of the IUD become substantially in the same orientation as the stem of the IUD. The orienting step ensures that the arms always fold above the orienting step in accordance with the downward triangular formation, and an upward triangular formation is prevented.

At this situation, the arms are captured in the far-end opening by manual maneuvering of the graduated tube. The maneuvering essentially involves partially withdrawing the graduated tube backwards out of the open channel of the downloading device, angularly lifting the graduated tube 16 above the open channel, slightly turning it axially on either side so as to make the ends of the arm of IUD enter the far-end opening of graduated tub and finally pushing up the graduated tube again. To take out the graduated tube along with captured IUD out of the downfolding device, the graduated tube is axially turned substantially by an angle of about 90 degrees, particularly 85 to 95 degrees on either side so that it can come out from the top of the downfolding device, clear of the projecting ridge.

The stopper is adjusted to the required location in accordance with the sounding measurement carried out independently, as is known.

The process thus far is carried out while the instrument is substantially inside the partially open transparent pouch.

The Instrument is now fully withdrawn from the pouch and inserted in uterus of the female till the stopper touches the external orifice of cervix of woman. The graduated tube is withdrawn, while the pushrod is kept steady, thereby first releasing the arms of the IUD and then the stem of the IUD from the graduated tube. The folded arms of IUD return to its original shape of the arms. The graduated tube is withdrawn out of the uterus. This two-stage withdrawal ensures that IUD is not disturbed by the withdrawal of the graduated tube.

Construction of the converging opening of the downfolding device is possible in different ways, by different radii or by providing a straight but angular slant, conceptually and eventually leading to folding of the arms of IUD at it is pushed inside the downfolding device.

As a variation, the maneuvering need not involve partially withdrawing of the graduated tube backwards out of the open channel of the downloading device, and the graduated tube may still be angularly lifted above the open channel, since the root thickness of the base in-between the open channel is minimal and consequently, the exit opening increases by the base flexing and or when a lower surface of the base is devoid of a firm support underneath.

BRIEF DESCRIPTION OF DRAWINGS

FIG. 5A is a front view of the downfolding device while

FIG. 9A is a sectional top view of the graduated tube with downfolded IUD therein in the downward triangular formation, and the graduated tube before loading an IUD, while

FIG. 10A-10E show steps, in perspective view, of preparing the instrument for insertion of the IUD, while

DETAILED DESCRIPTION OF INVENTION

Preferred embodiment of an instrument to load and insert a downfoldable intra-uterine device and process thereof according to present invention will now be described in detail, with reference to the accompanying drawings. The terms and expressions which have been used here are merely for description and not for limitation. The term "preparing" and "loading" are used interchangeably.

Figure 1:
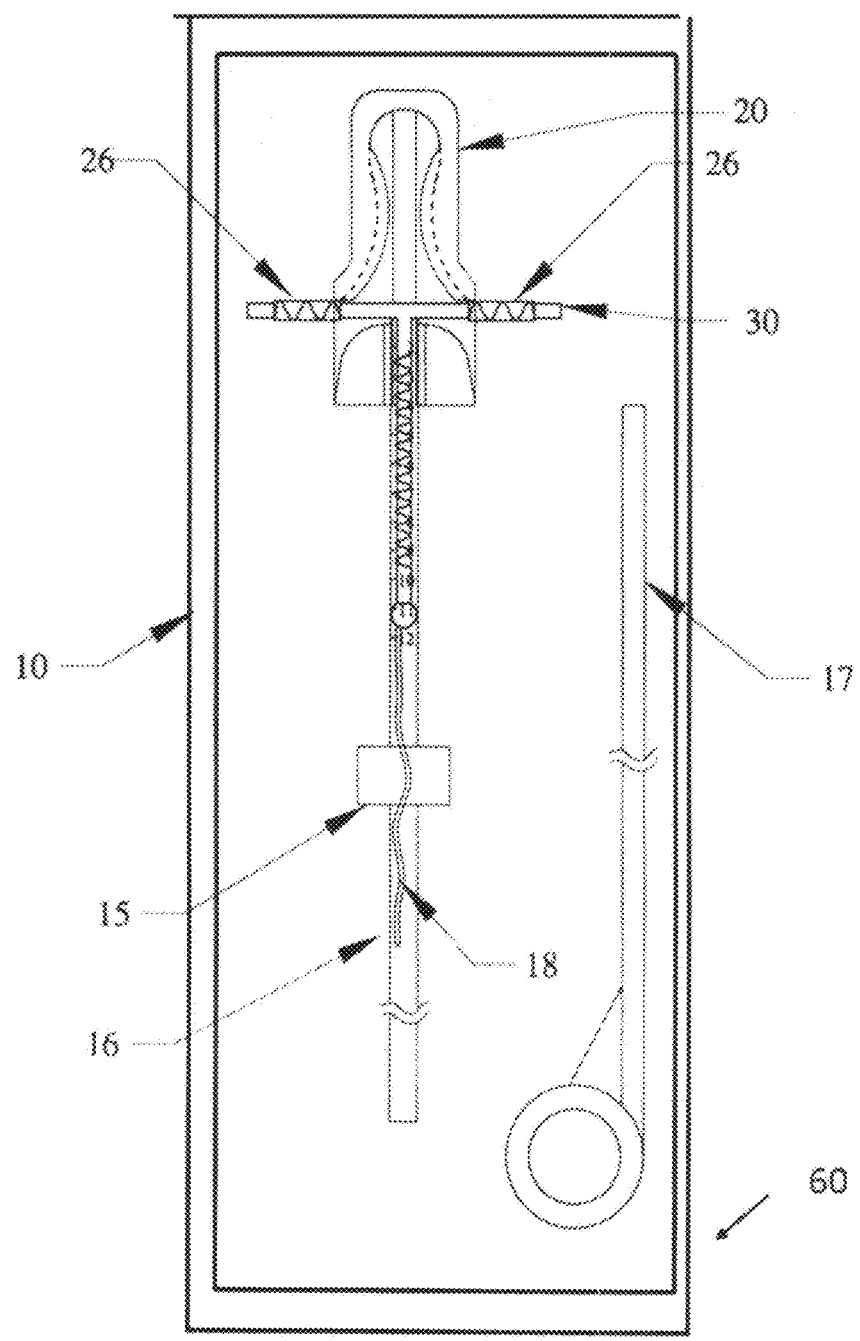
FIG. 1 is a front view of an apparatus as per present invention.

FIG. 1, the instrument 10 according to present invention comprises a downfolding device 20, a graduated tube 16, a push rod 17, a stopper 15, and an IUD 30, encased in a transparent pouch 60.

Figure 2:
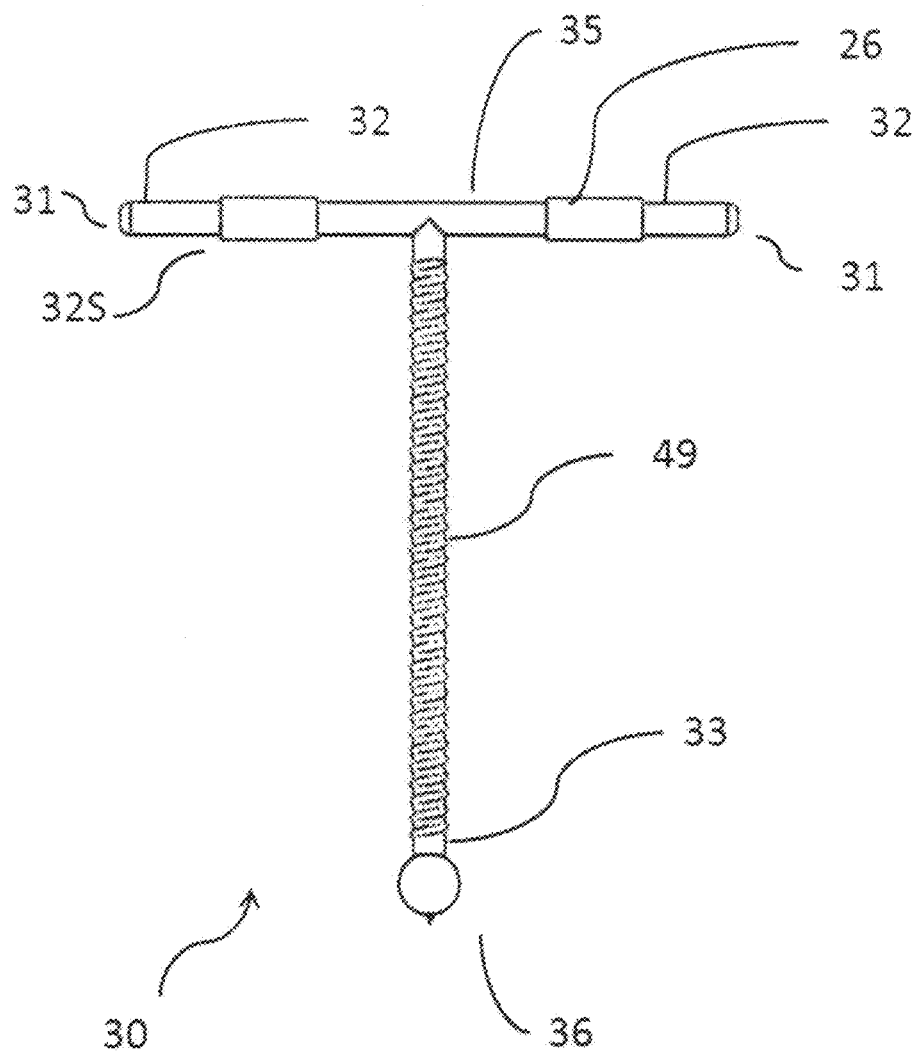
FIG. 2 is a front view of a downfoldable IUD.

FIG. 2, the IUD 30 is essentially in a "T" shape, comprising a moulded frame 35 having a metallic envelope/wire 49 wrapped around a stem 33, preferably with a sleeve 26 on each of a pair of arms 32. The sleeve 26 is generally made of medical grade copper.

Figure 3:
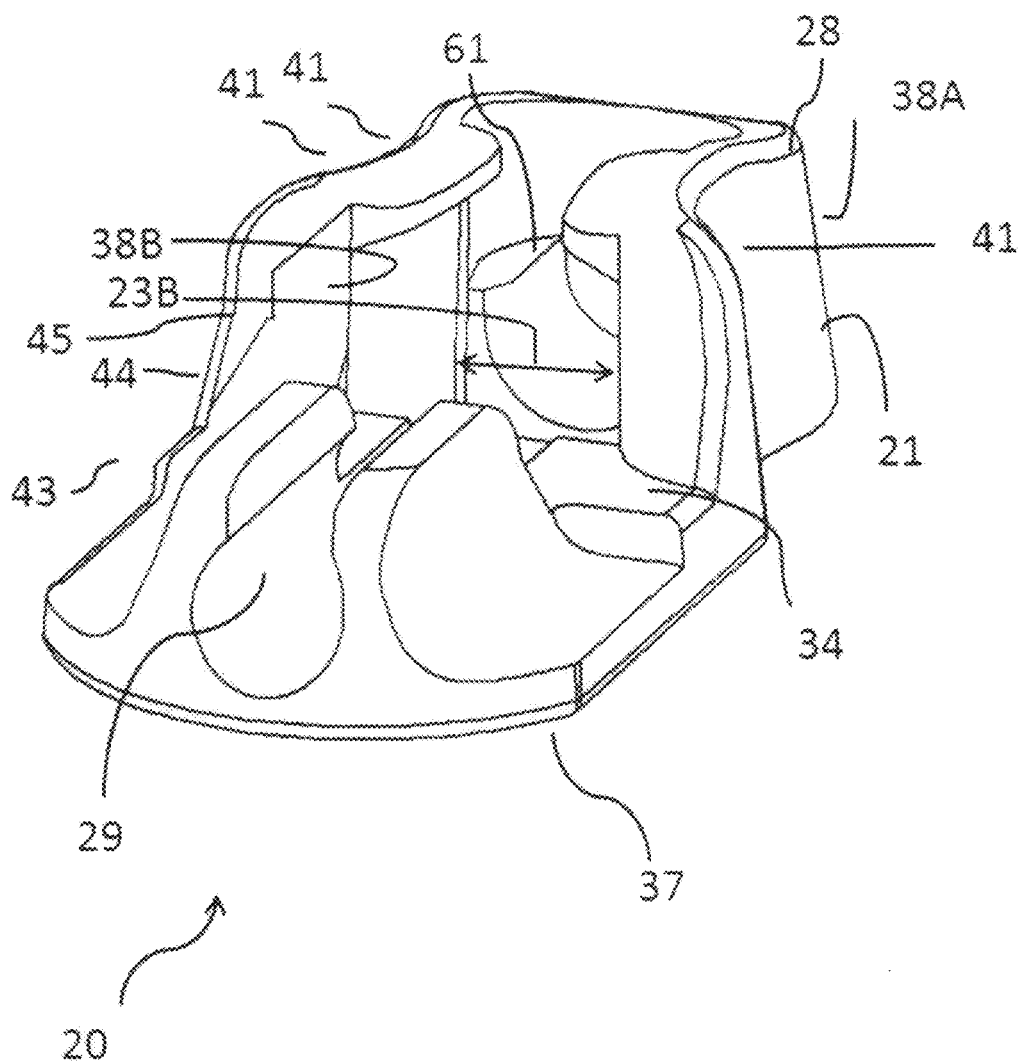
FIG. 3 is a perspective view of a downfolding device as per present invention.
Figure 4:
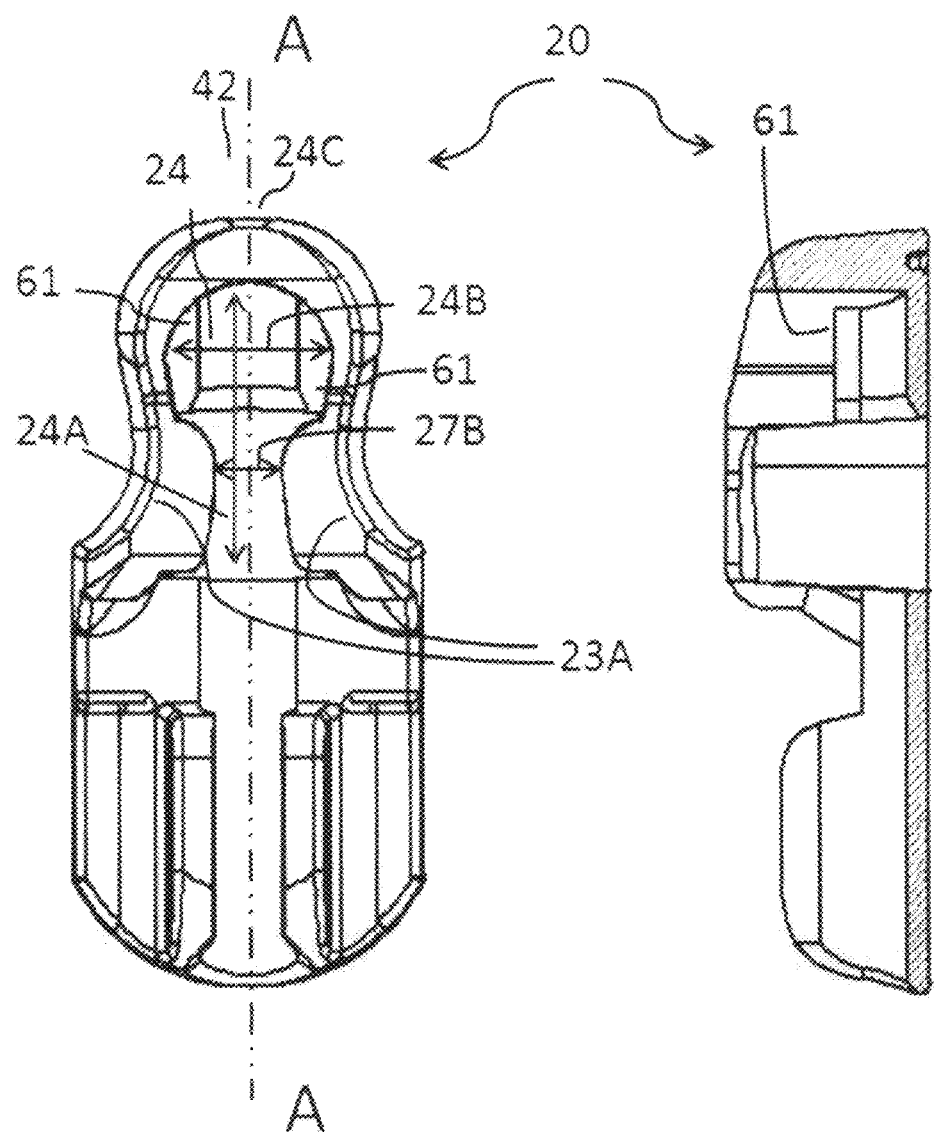
FIG. 4 is a top view and a sectional side view of the downfolding device.
Figure 5A:
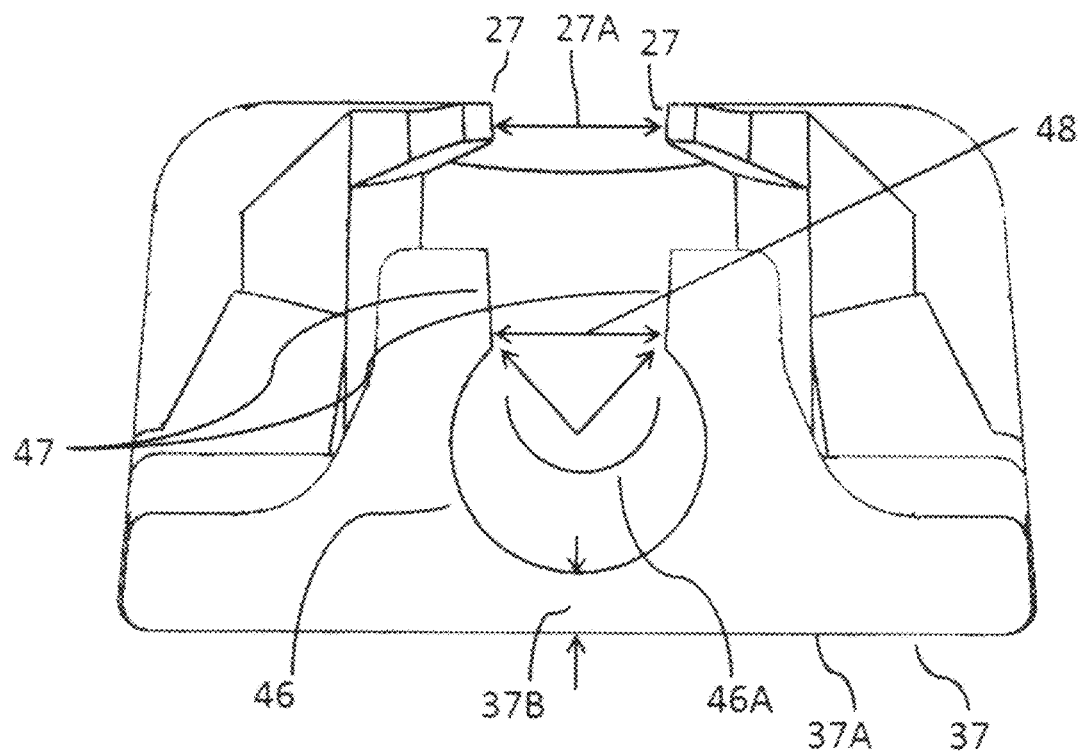

FIGS. 3, 4, 5A, the downfolding device 20 has a fence 21 and an open channel 29, spaced by a platform 34, on a base 37. An external side 38A of the fence 21 has a depression 41 on either side, a concave, and generally complementary to a convex shape of human thumb and human fingers and therefore acts as a receptacle; consequently a service provider can hold the downfolding device 20 firmly and which facilitates easy and secure loading of IUD into the graduated tube 16. An internal side 38B of the fence 21 has a converging opening 23A, turning into a narrow zone 23B and ending into a well 24 having a depth 24A.

Figure 5B:
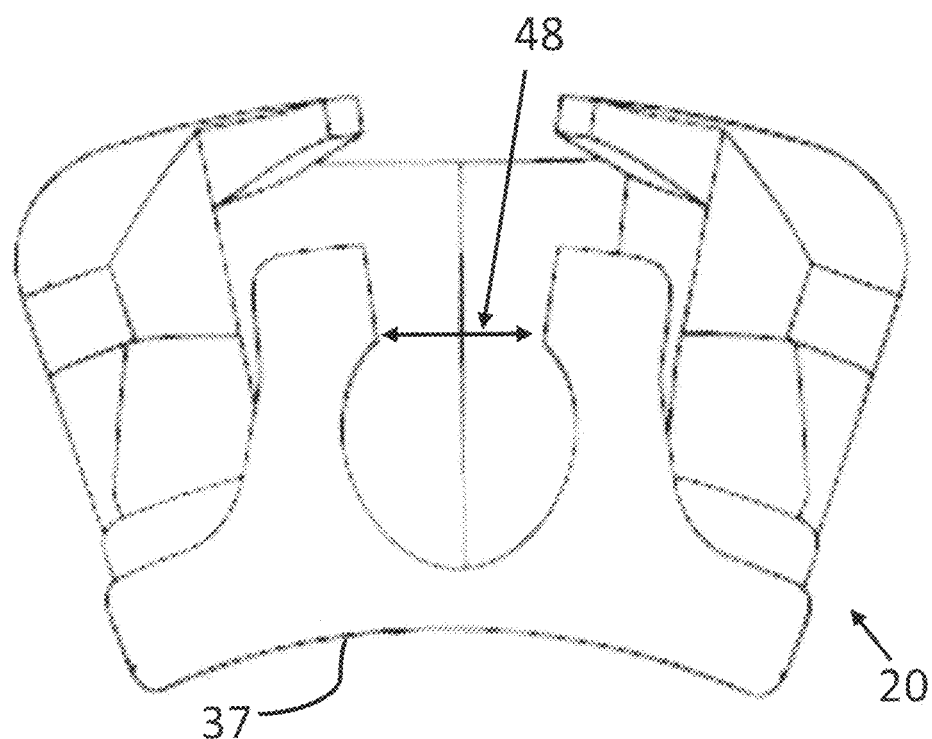
FIG. 5B is another front view with its base flexed.

The narrow zone 23B has a projecting ridge 27 on either side, leaving a clear passage 27A. The well 24 has an orienting step 61 on either side. The well 24 is closed from a far end 42. A proximal end 43 of the converging opening has, on either side, an inclined wall 44 with a local relief 45, for accommodating a step 32S in the arms 32 of the IUD 30 which may be due to the sleeve 26, and merging with the internal side 38B of the fence 21. A diametric dimension 24B of well 24, above the orienting step 61, is commensurate with an envelope dimension 38 of the IUD 30 when downfolded. The open channel 29 has a circular orifice 46 having a sector of angle measure 46A at least 220°. The circular orifice 46 merges with a pair of divergent walls 47, having an exit opening 48 that is initially marginally less than an external diameter 22B of the graduated tube 16. A root thickness 37B of the base 37 in-between the open channel 29 is minimal. Consequently, the exit opening 48 increases by the base 37 flexing and or when a lower surface 37A of the base 37 is devoid of a firm support underneath as particularly shown in FIG. 5B. An upper enveloping surface 28 all over the downfolding device 20 is a smoothened surface devoid of sharp projection.

A width 27B of the clear passage 27A is comparable to a height 22C of a triangle (FIG. 9A) formed at a far end of the graduated tube 16 carrying a prepared IUD, as described below.

Figure 6:
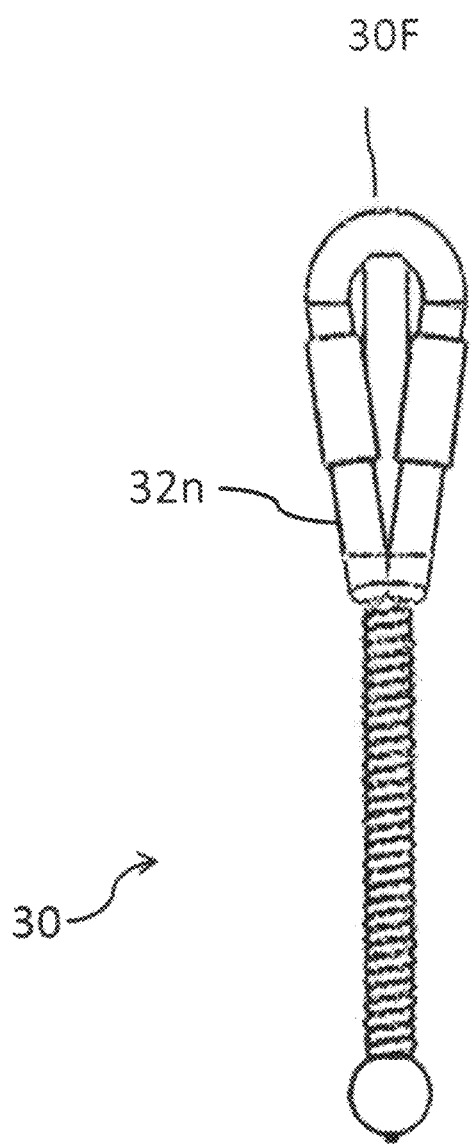
FIG. 6 is a front view of a downfolded IUD with arms downfolded.
Figure 7:
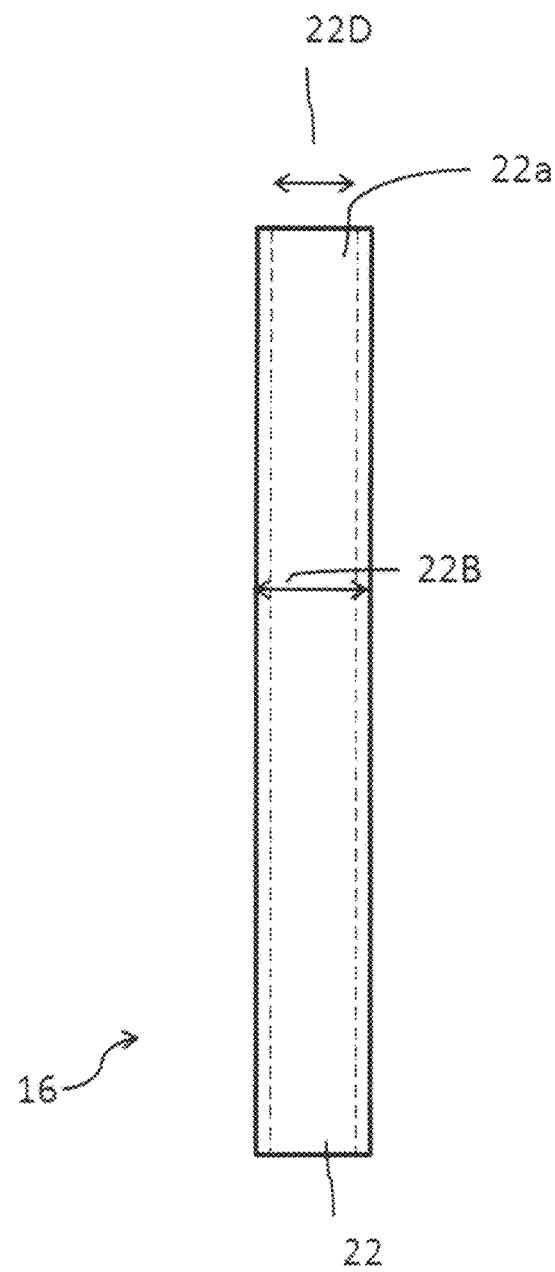
FIG. 7 is a front view of a graduated tube.
Figure 8:
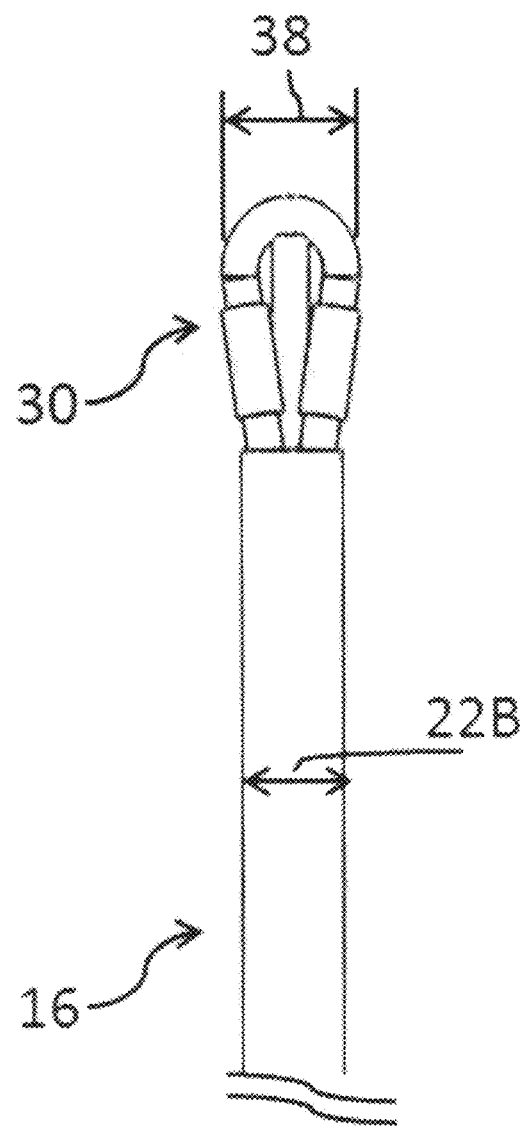
FIG. 8 is a partial front view of a prepared IUD.

FIGS. 6, 7 and 8, the graduated tube 16 has an internal diameter 22D of a far-end opening 22a of the graduated tube 16 just sufficient to capture the stem 33 and both arms 32 of IUD in substantially a downward triangular formation 51. The downward triangular formation 51 is attainable by entering the IUD 30 with a downfolded arms 32n in a graduated tube 16 from the stem end 36 such that the arm ends 31 subsequently enter the graduated tube 16 with a minimal force such that the arm ends 31 are inside a graduated tube 16 up to the step 32S of the sleeve 26 on the IUD 30. Also, the graduated tube 16 is provided with measurement marks 14 so that the stopper 15 can be conveniently adjusted at precisely required position without needing measurement device and while the instrument 10 is in the transparent pouch 60.

The IUD 30 is parked in the downfolding device 20 with its arms 32 resting at the platform 34 and the stem 33 passing through the open channel 29 of the downfolding device 20. The IUD 30 is parked in the downfolding device 20 in the "T" shape which it is required to maintain inside uterus 50.

The downfolding device 20 is firmly disposed in a prescribed place in the transparent pouch 60. The prescribed place in the transparent pouch 60 is ensured by a tight fit of the downloading device 20 in the transparent pouch 60; or by thermally shrinking the thermoplastic sheath 39 around the downfolding device 20. As another embodiment, the prescribed place in the transparent pouch 60 is by a glue disposed between the base 37 of the downfolding device 20 and the back 40 of the transparent pouch 60.

The instrument 10 is packaged in sterile environment in the transparent pouch with a transparent cover 39 and a back 40. As a variation, the packaged instrument 10 is sterilized after packaging.

Figure 11:
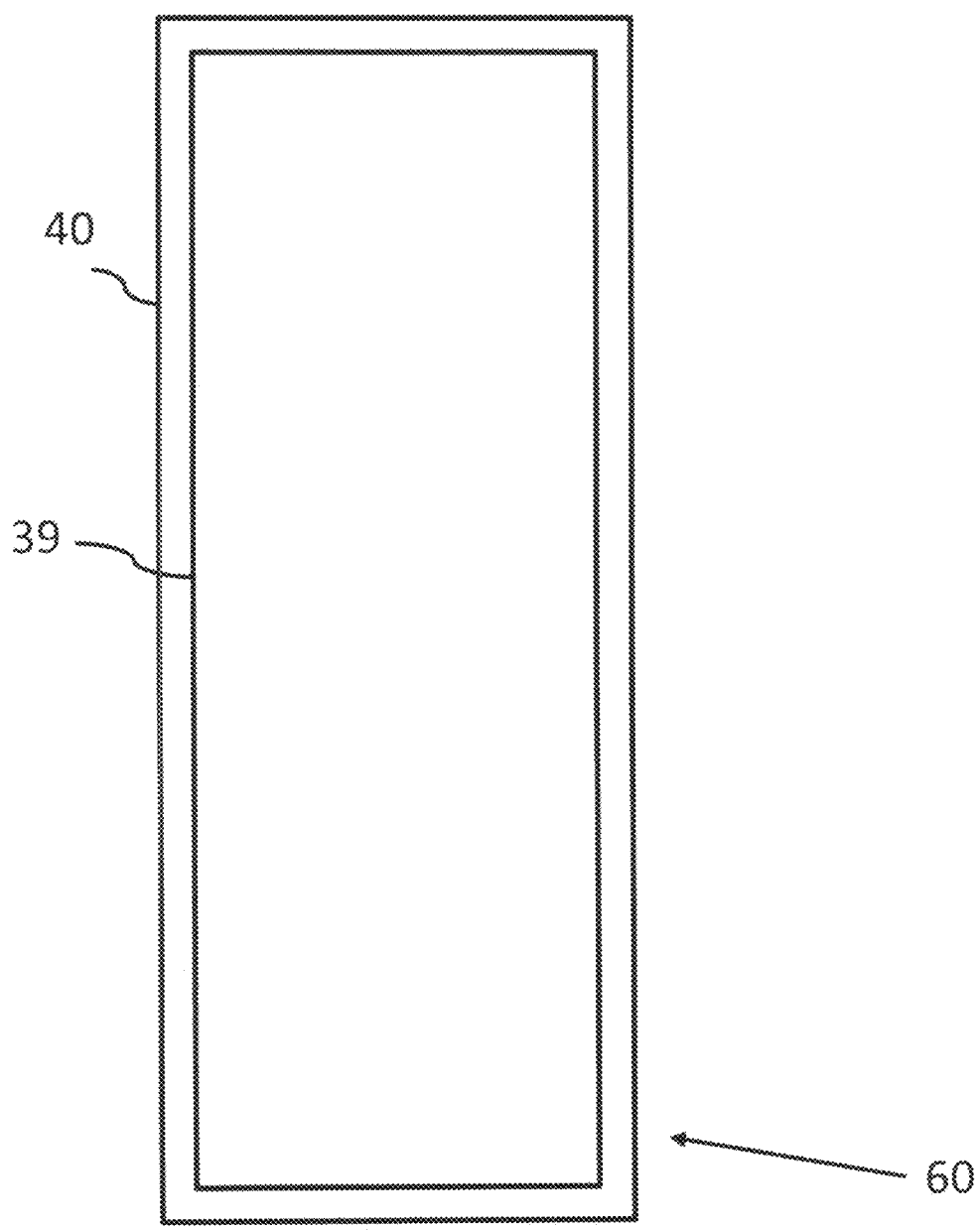
FIG. 11 is a representative view of a transparent pouch.

FIG. 11, the transparent pouch 60 is made of a thermoplastic sheath of thickness such that the downfolding device 20 when gripped firmly from an outside of the transparent cover 39 of the transparent pouch 60 can be gripped adequately. The upper enveloping surface 28 all over the downfolding device 20, being a smoothened surface devoid of sharp projection, facilitates such ripping without the thermoplastic sheath getting punctured or torn consequently. A shear strength of the thermoplastic sheath withstands expected transportation and storage abuse.

FIG. 10A-10E, to start the process of loading, the transparent cover 39 is partially separated (not explicitly shown such in these views) from the back 40 of the transparent pouch 60, only to be able to access and hold the near end opening 22 of graduated tube 16.

The downfolding device 20 is firmly held by one hand from outside the transparent cover 39 while the graduated tube 16 is pushed in. As a variation, the transparent pouch 60 is firmly held instead of the downfolding device 20.

Figure 12:
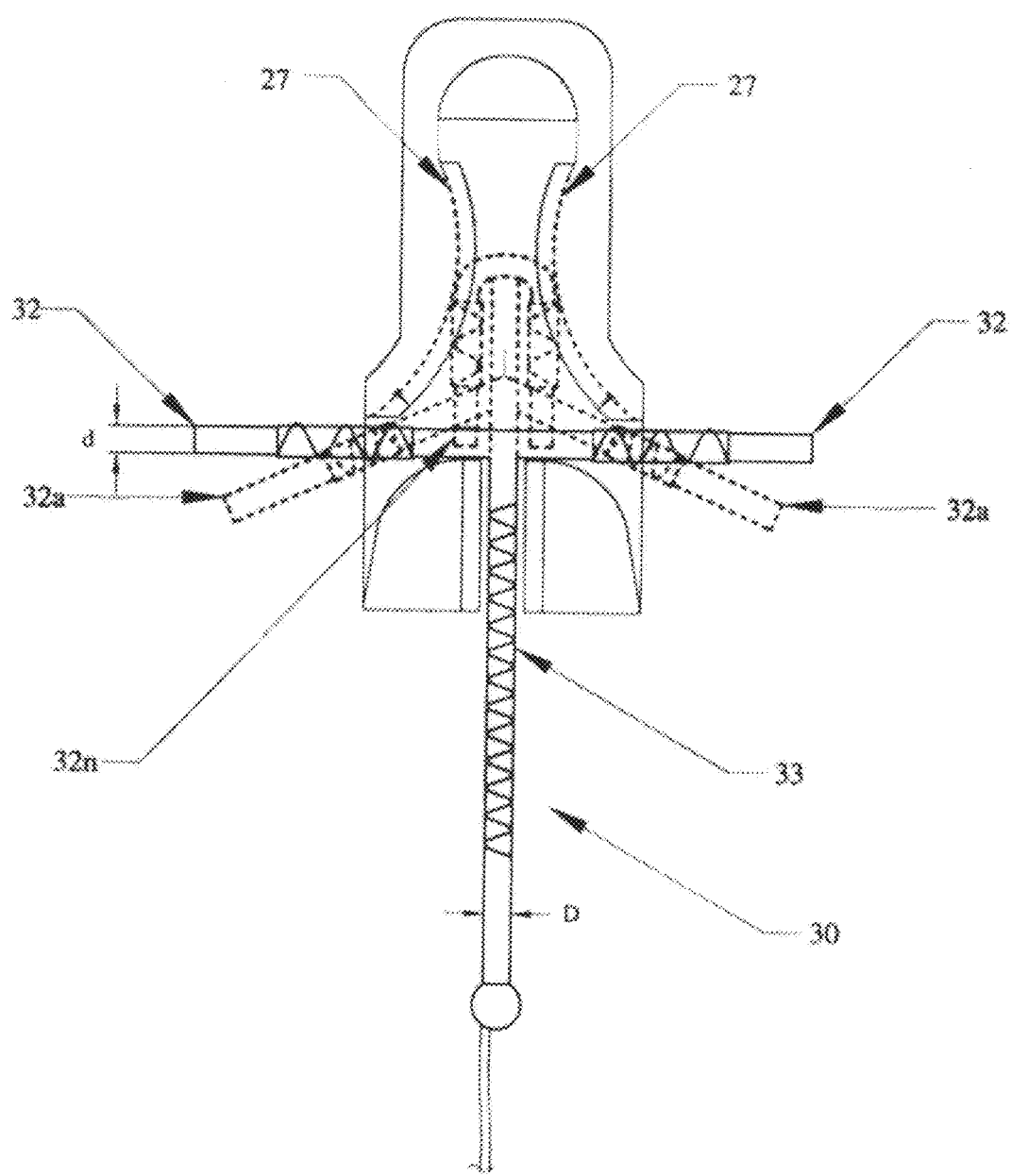
FIG. 12 is a representative top view of a downfolding device and the IUD in two different shapes while loading.

As the graduated tube 16 starts pushing the IUD 30, the IUD 30 has to negotiate its shape due to the converging opening 23A in the downfolding device 20. Consequently, the arms 32 of the IUD 30 start folding towards the stem end 36, such partially folded arms 32a (FIG. 12). The downfolding device 20 guides the graduated tube 16 through towards the well 24 consequent to the open channel 29.

Figure 9A:
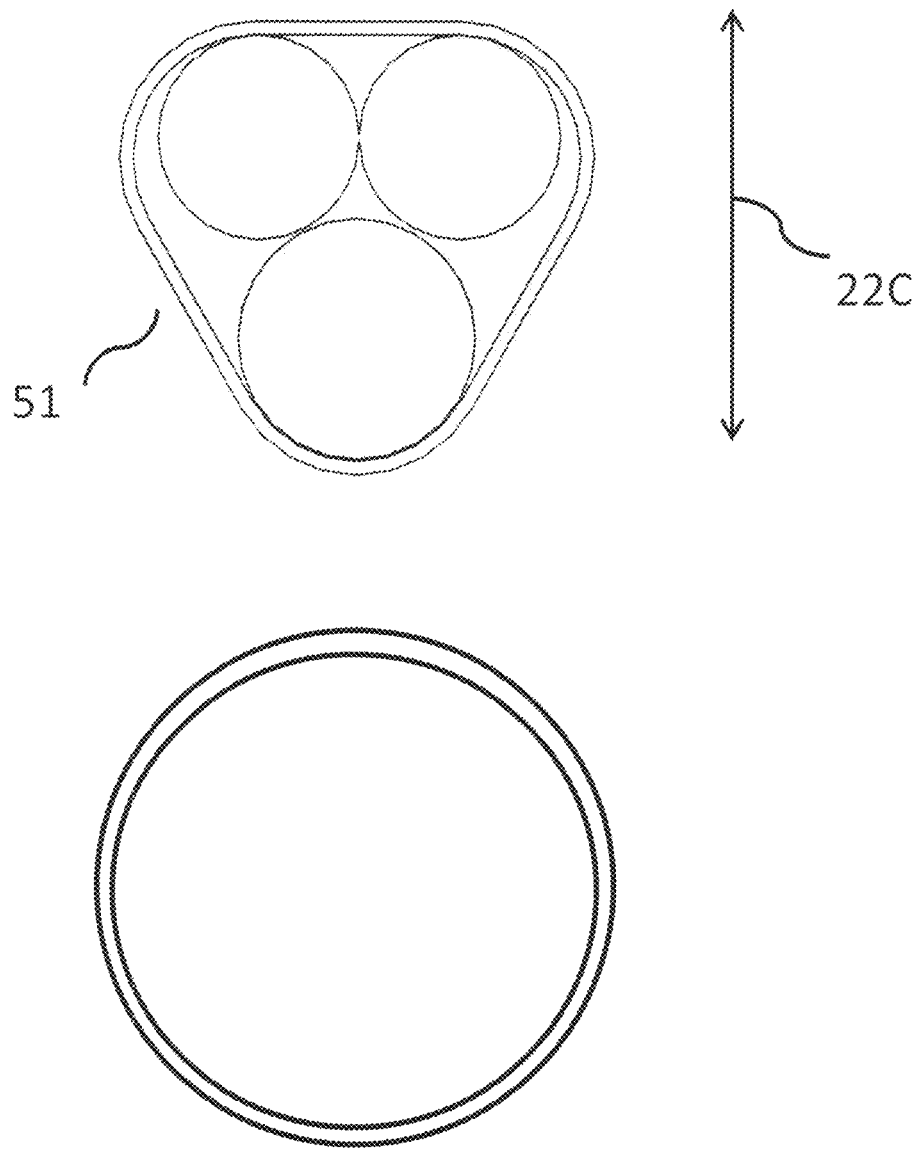
Figure 9B:
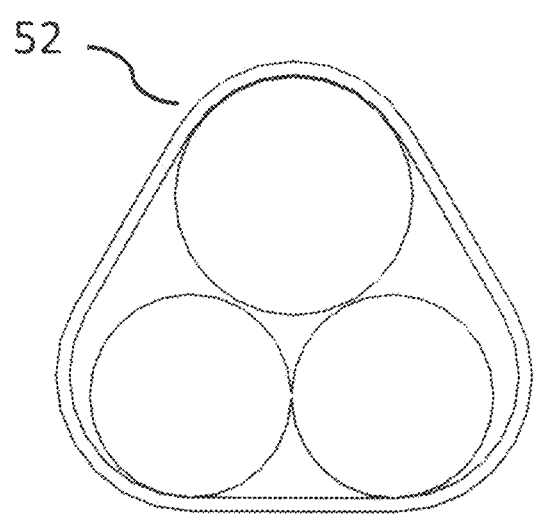
FIG. 9B is a similar sectional top view in the upward triangular formation.

The depth of the well 24A of the well 24 of the downfolding device 20 is such that, as the graduated tube 16 continues to push the IUD 30, there comes a situation when a fundal end 32F 30F of the IUD 30 gets stopped by the end 24C of the well 24, and the arms 32n of the IUD 30 become substantially in the same orientation as the stem 33 of IUD 30. The orienting step 61 ensures that the arms 32 always fold above the orienting step 61 in accordance with the downward triangular formation 51, and an upward triangular formation 52 is prevented (FIG. 9A, 9B).

Figure 10A:
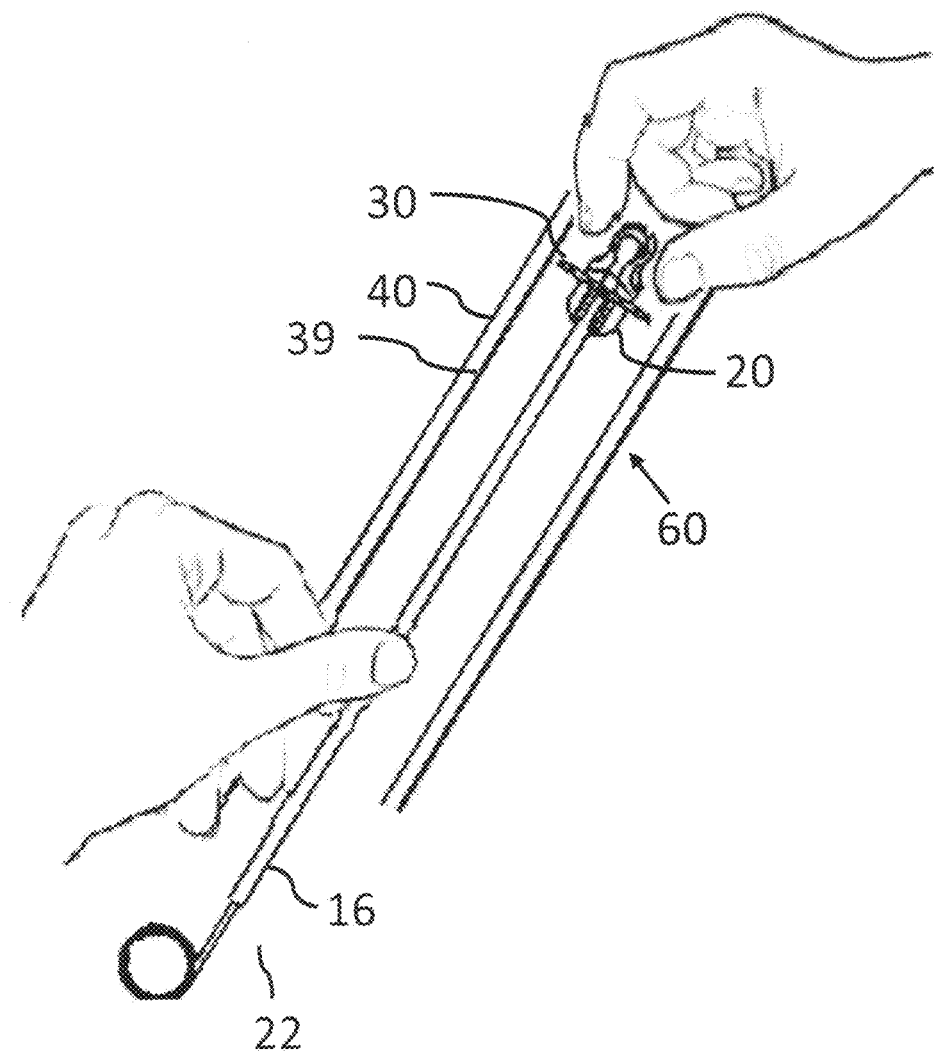
Figure 10B:
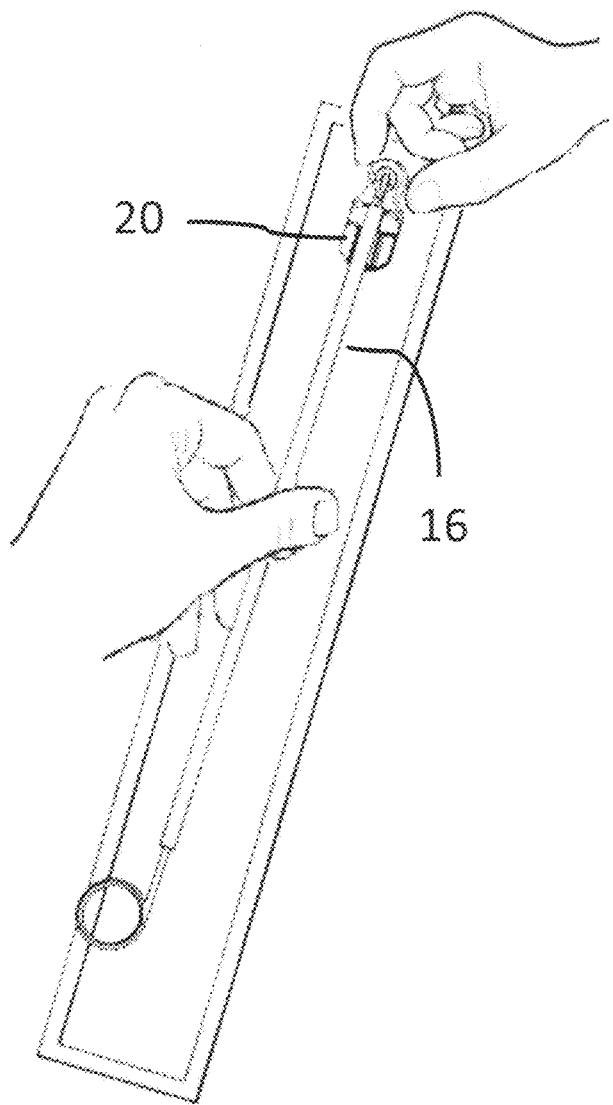
Figure 10C:
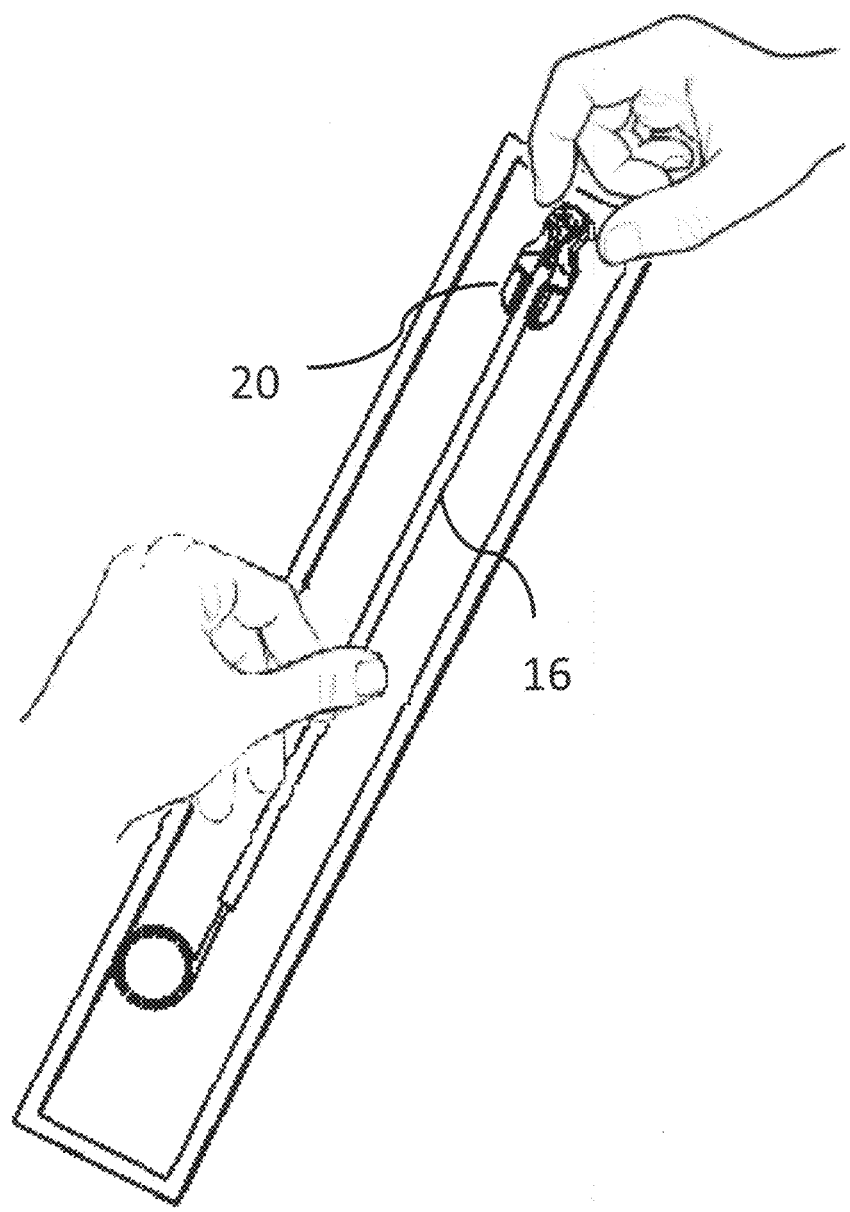
Figure 10D:
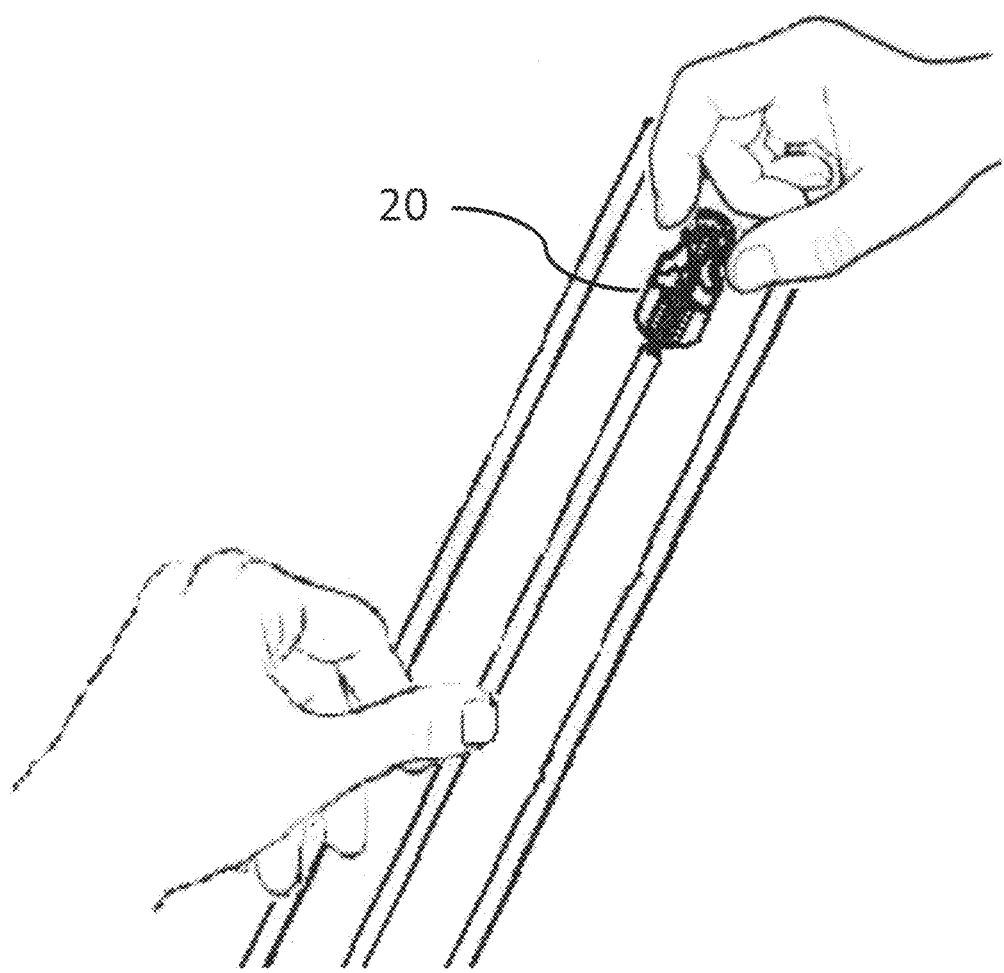
Figure 10E:
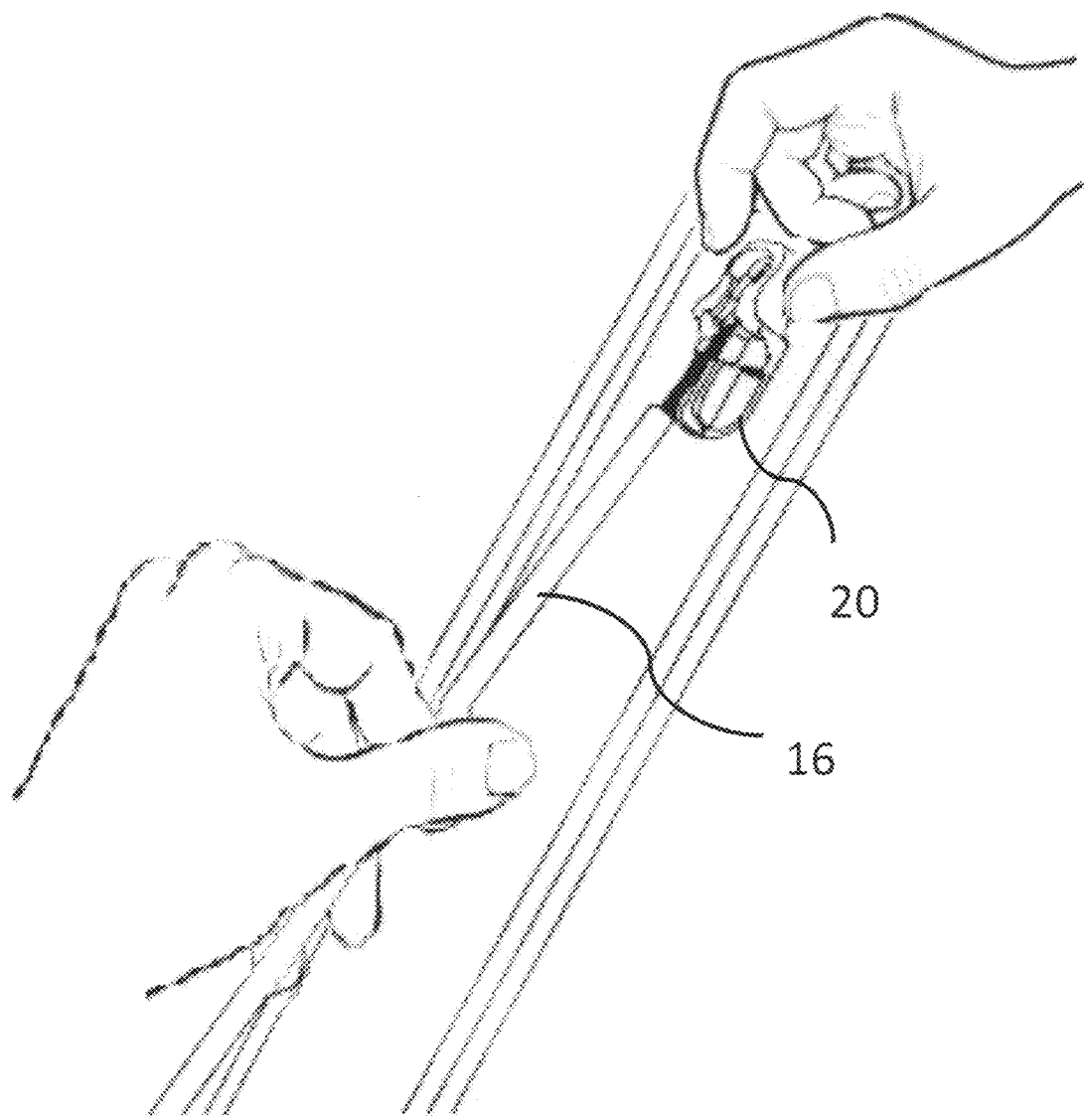
Figure 10F:
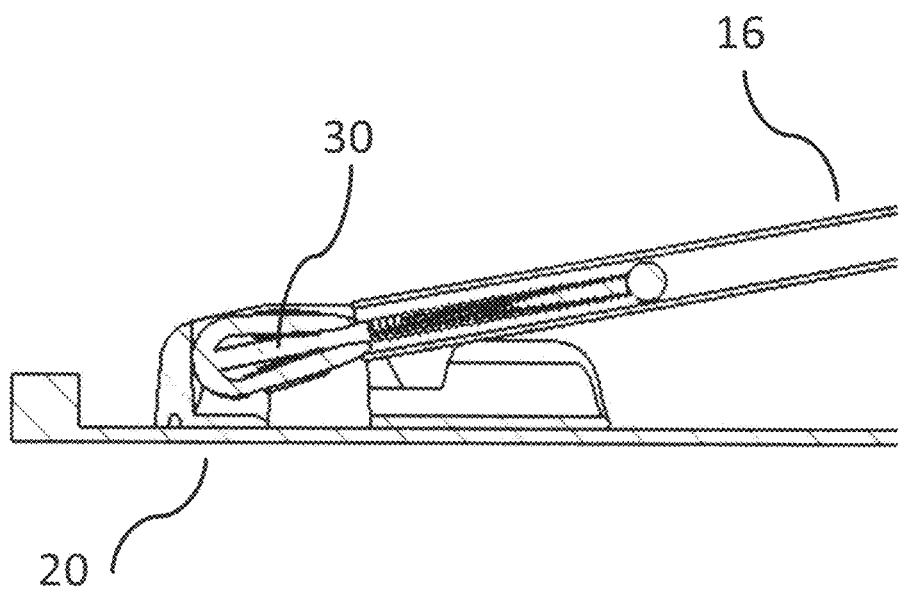
FIG. 10F is a sectional side view.

At this situation, the arms 32 are captured in the far-end opening 22a by manual maneuvering of the graduated tube 16. The maneuvering essentially involves partially withdrawing the graduated tube 16 backwards out of the open channel 29 of the downloading device 20, angularly lifting the graduated tube 16 above the open channel 29, slightly turning it axially on either side so as to make the ends of the arm 32n (FIG. 12) of IUD 30 enter the far-end opening 22a of graduated tube 16 and finally pushing up the graduated tube 16 again. FIG. 10F, to take out the graduated tube 16 along with the captured IUD 30 out of the downfolding device 20, the graduated tube 16 is axially turned substantially by about 90 degrees on either side so that it can come out from the top of the downfolding device 20, clear of the projecting ridge 27.

The stopper 15 is adjusted to the required location 12 in accordance with the sounding measurement carried out independently, as is known.

The process thus far is carried out while the instrument is substantially inside the partially open transparent pouch 60. Consequently, the process is without direct manual touching and is therefore hygienic.

Figure 13:
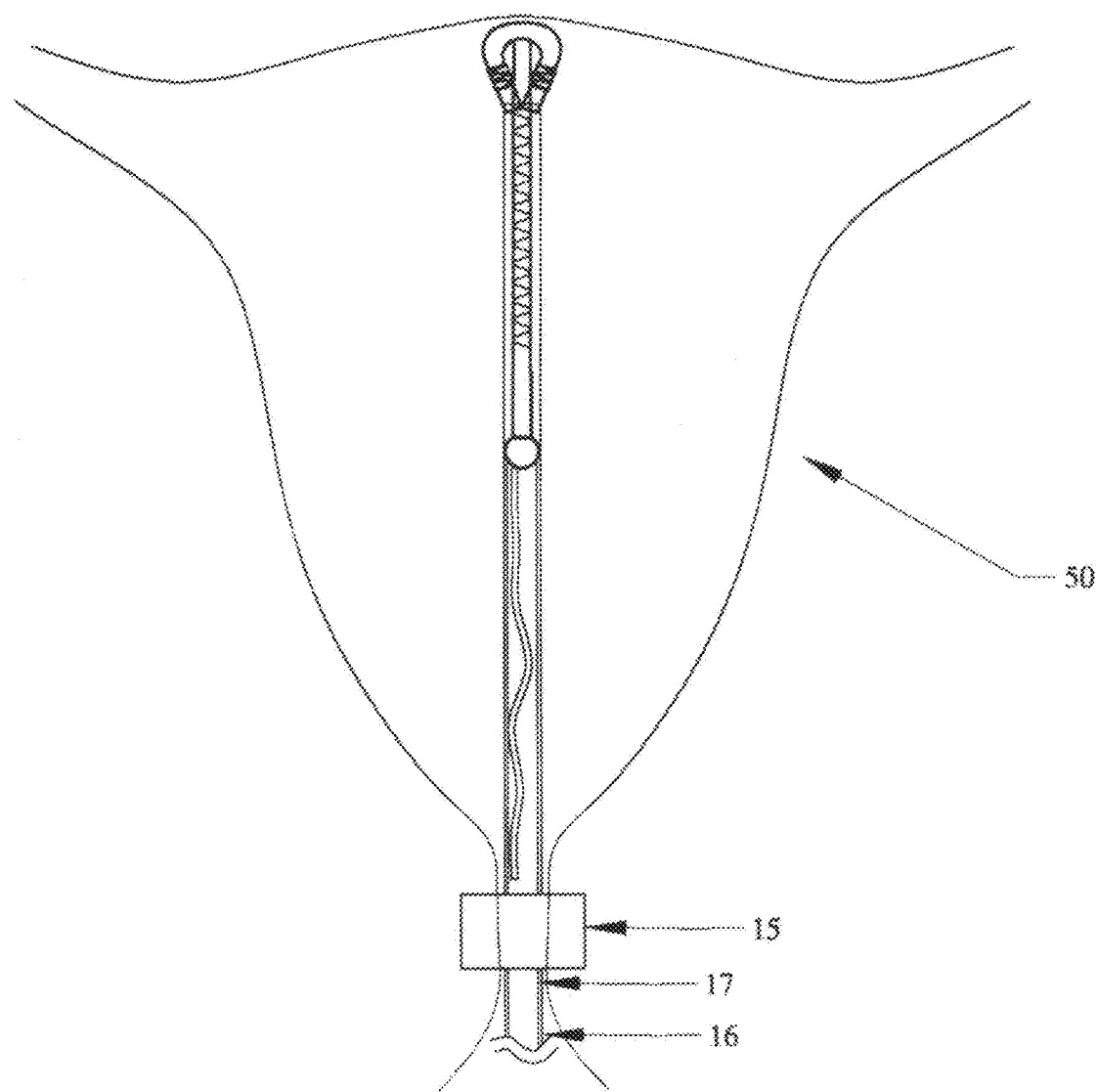
FIG. 13 shows a simplified uterus with IUD inserted.
Figure 14:
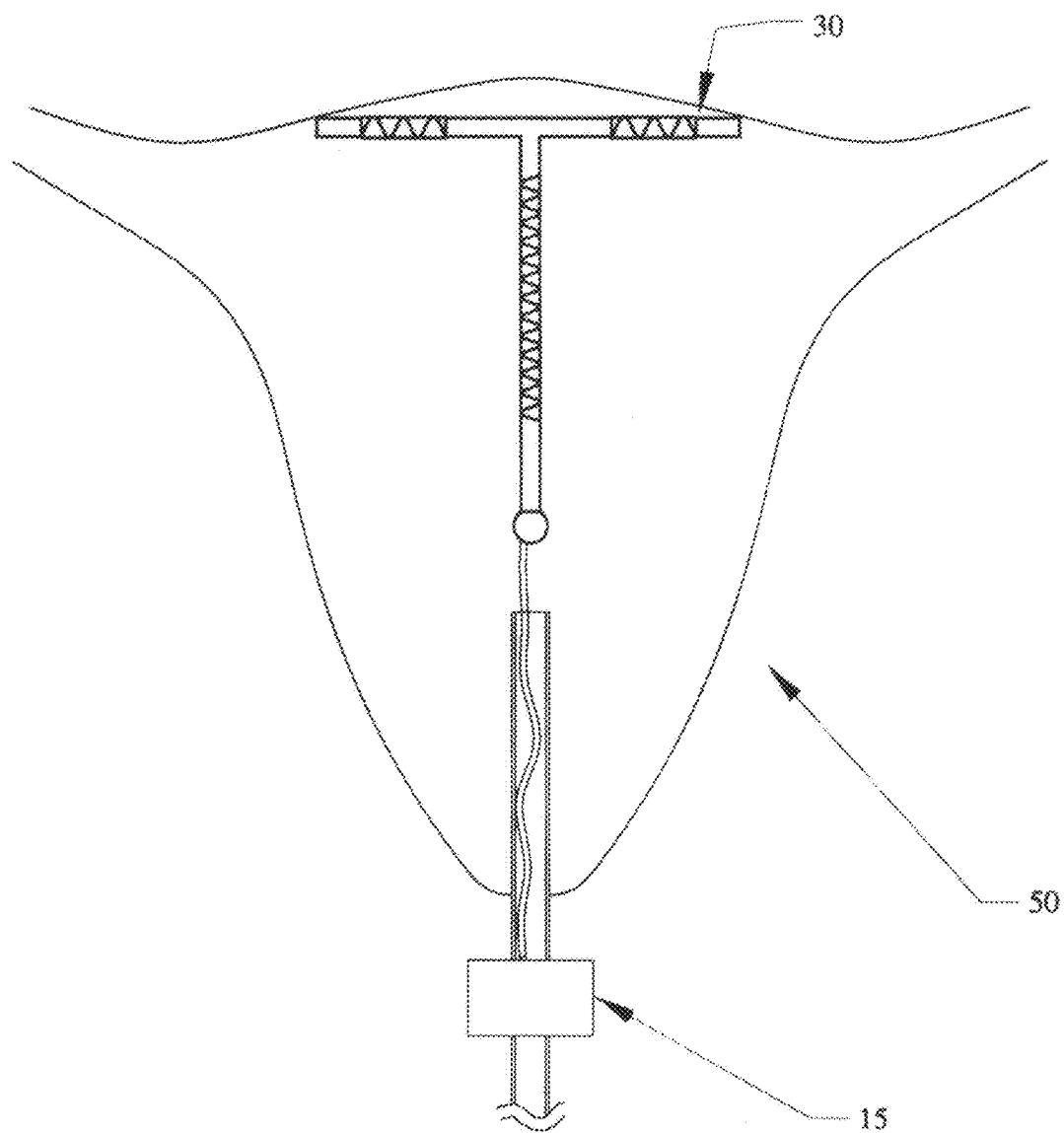
FIG. 14 shows a simplified uterus with IUD placed.

FIGS. 13, 14, the Instrument 10 is now fully withdrawn from the pouch and inserted in uterus 50 of the female till stopper 15 touch the external orifice of cervix. The graduated tube 16 is withdrawn, while the pushrod 17 is kept steady, thereby first releasing the arms 32n of the IUD 30 and then the stem 33 of the IUD 30 from the graduated tube 16. The folded arms 32n of IUD 30 return to its original shape of the arms 32. The graduated tube 16 is withdrawn out of the uterus 50. This two-stage withdrawal ensures that the IUD 30 is not disturbed by the withdrawal of the graduated tube 16.

Construction of the converging opening 23A of the downfolding device 20 is possible in different ways, by different radii or by providing a straight but angular slant, conceptually and eventually leading to folding of the arms 32 of IUD 30 at it is pushed inside the downfolding device 20.

As a variation, the maneuvering need not involve partially withdrawing of the graduated tube 16 backwards out of the open channel 29 of the downloading device 20, and the graduated tube 16 may still be angularly lifted above the open channel 29, since the root thickness 37B of the base 37 in-between the open channel 29 is minimal and consequently, the exit opening 48 increases by the base 37 flexing and or when a lower surface 37A of the base 37 is devoid of a firm support underneath.

I claim:

1. An instrument (10) to prepare an intra-uterine device 30 for insertion in uterus (50) of a woman, the instrument (10) comprising a downfolding device (20), a graduated tube (16), a push rod (17), a stopper (15), and an IUD (30), encased in a transparent pouch (60), characterized in that the downfolding device (20) has
   a fence (21) and an open channel (29), spaced by a platform (34), on a base (37),
   an external side (38A) of the fence (21) having a depression (41) on either side, a concave, that is adapted to be complementary to a convex shape of human thumb and human fingers,
   an internal side (38B) of the fence (21) having a converging opening (23A), turning into a narrow zone (23B) and ending into a well (24) having a depth (24A), the narrow zone (23B) having a projecting ridge (27) on either side and radially outward from the well (24), leaving a clear passage (27A), the well (24) having an orienting step (61) on either side, the well (24) closed from a far end (42), and including a diametric dimension (24B) above the orienting step (61) commensurate with an envelope dimension (38) of the IUD (30) when downfolded within well (24), and which ensures that the arms (32) of the IUD (30) always fold above the orienting step (61) in a downward triangular formation (51), and an upward triangular formation (52) is prevented,
   a proximal end (43) of the converging opening (23A) having, on either side, an inclined wall (44) with a local relief (45) merging with the internal side (38B) of the fence (21),
   the open channel (29) of a circular orifice 46 having a sector of angle measure (46A) at least 220°, the circular orifice (46) merges with a pair of divergent walls (47), having an exit opening (48) that is initially marginally less than an external diameter (22B) of the graduated tube (16),
   a root thickness (37B) of the base (37) in-between the open channel (29) and connecting the pair of divergent walls (47) is such that the exit opening (48) increases by the base (37) flexing below and parallel to the open channel (29) permitting withdrawal of the graduated tube (16) through an increased exit opening (48),
   an upper enveloping surface (28) all over the downfolding device (20) a smoothened surface devoid of sharp projection,
   a width (27B) of the clear passage (27A) comparable to a height (22C) of a triangle formed at a far end of the graduated tube (16), permitting removal of a captured IUD (30) with both arm ends (31) touching each other in a triangular formation (51, 52) with the stem (33), clear of the projecting ridge (27) and the graduated tube (16) angularly lifted above the open channel (29), and
   a depth (24A) of the well (24) such that as the IUD (30) is pushed into the downloading device (20), a fundal end (30F) of the IUD (30) gets stopped by the end (24C) of the well (24), and an arms (32n) of the IUD (30) become substantially in the same orientation as the stem (33) of IUD (30) while the orienting step (61) causes the arms (32) to fold above the orienting step (61);
   the graduated tube (16) has an internal diameter (22D) of a far-end opening (22a) of the graduated tube (16) sufficient to capture the stem (33) and both arms (32) of the IUD (30) with both arm ends (31) touching each other in a triangular formation (51, 52) with the stem (33);
   the transparent pouch (60) has a thermoplastic sheath (39) of a prescribed flexibility, and a back (40); and
   the IUD (30) is parked in the downfolding device (20) with its arms (32) resting at the platform (34) and the stem (33) passing through the open channel (29) of the downfolding device (20), the IUD (30) is parked in the downfolding device 20 in the "T" shape which it is required to maintain inside uterus (50), the downfolding device (20) is firmly disposed in a prescribed place in the transparent pouch (60).

2. The instrument (10) to prepare the intra-uterine device 30 for insertion as claimed in claim 1, wherein the prescribed place in the transparent pouch (60) is by thermally shrinking the thermoplastic sheath (39) around the downfolding device (20).

3. The instrument (10) to prepare the intra-uterine device 30 for insertion as claimed in claim 1, wherein the prescribed place in the transparent pouch (60) is by a glue disposed between the base (37) of the downfolding device (20) and the back (40) of the transparent pouch (60).

4. A method to prepare an instrument (10) with an intra-uterine device (30) for insertion in uterus (50) of a woman, the instrument comprising of a downfolding device (20), a graduated tube (16), a push rod (17), a stopper (15), and an IUD (30), encased in a transparent pouch (60) having a back (40); the method comprising the steps of:
   Separating partially a transparent cover (39) of the transparent pouch (60) from the back (40) of the transparent pouch (60), only to be able to access and hold a near-end opening (22) of the graduated tube (16),
   Holding firmly the downfolding device (20) by one hand from outside the transparent cover (39),
   Pushing in the graduated tube (16) in the downfolding device (20) within and along the open channel (29),
   Pushing in the IUD (30) by the graduated tube (16),
   Folding of the arms (32) of the IUD (30) towards a stem end (36) of the IUD (30), resulting into such partially folded arms (32a) of the IUD (30),
   Withdrawing the graduated tube (16) backwards till the graduated tube (16) is just free from an open channel (29) of the downfolding device (20),
   Lifting the graduated tube (16) angularly about a fundal end (30F) of the IUD (30) out of an increased exit opening (48) out of, above and non-parallel to the open channel (29),
   Pushing in again the graduated tube (16) towards the IUD (30) capturing an ends of the arm (32n) of IUD (30) such that the ends of the arms (32n) of the IUD (30) enter a far-end opening (22a) of graduated tube (16),
   Further pushing in the graduated tube (16) till the fundal end (30F) of the IUD (30) gets stopped by an end (24C) of a the well (24) of the downfolding device (20),
   Turning axially the graduated tube (16) by 85 to 95 degrees on either side,
   Taking out the graduated tube (16) completely out of the downfolding device (20) and the transparent pouch (60) along with the IUD (30).

5. The method to prepare the instrument (10) with the intra-uterine device (30) as claimed in claim 4, wherein the capturing an ends of the arm (32*n*) of IUD (30) is in a downward triangular formation (51).

6. The method to prepare the instrument (10) with the intra-uterine device (30) as claimed in claim 4, wherein the lifting of the graduated tube (16) angularly above the open channel (29), without withdrawing the graduated tube (16) backwards till the graduated tube (16) is just free from the open channel (29), is enabled by an the exit opening (48) of the downfolding device (20) increasing by a base (37) of the downfolding device (20) flexing when a lower surface (37A) of the base (37) is devoid of a firm support underneath.

7. The method to prepare the instrument (10) with the intra-uterine device (30) as claimed in claim 4, wherein the holding firmly the downfolding device (20) is by firmly holding the transparent pouch (60).

8. The method to prepare the instrument (10) with the intra-uterine device (30) as claimed in claim 7, wherein the transparent pouch (60) is firmly disposed on a surface.

\* \* \* \* \*